United States Patent [19]

Paulke et al.

[11] 4,197,641

[45] Apr. 15, 1980

[54] ELECTRICAL PULP TESTING INSTRUMENT

[75] Inventors: Monika Paulke, Neunkirchen a.Brand; Eugen Hohmann, Heppenheim; Bernd Nickel, Bensheim, all of Fed. Rep. of Germany

[73] Assignee: Siemens Aktiengesellschaft, Berlin & Munich, Fed. Rep. of Germany

[21] Appl. No.: 890,635

[22] Filed: Mar. 20, 1978

[30] Foreign Application Priority Data

Mar. 30, 1977 [DE] Fed. Rep. of Germany ....... 2714192

[51] Int. Cl.² ............................................ A61C 19/04
[52] U.S. Cl. ..................................... 433/32; 128/741
[58] Field of Search ............... 128/2.1 R, 211 C, 2 R, 128/2 N, 2 S, 404, 405, 407–411, 419 R, 419 D, 419 S, 421–423, 2.06 F; 32/40 R, 1; 128/741, 776, 787, 800, 801

[56] References Cited

U.S. PATENT DOCUMENTS

| | | | |
|---|---|---|---|
| 2,204,295 | 6/1940 | Brockman | 128/2.1 R |
| 2,522,052 | 9/1950 | Logan et al. | 128/2.1 R |
| 3,128,759 | 4/1964 | Bellis | 128/2.1 R |
| 3,794,022 | 2/1974 | Nawracaj et al. | 128/422 |
| 3,886,950 | 6/1975 | Ukkestad et al. | 128/419 D |
| 3,921,624 | 11/1975 | Vogelman | 128/2.06 F |
| 3,933,147 | 1/1976 | DuVall et al. | 128/408 |
| 3,943,919 | 3/1976 | Landgraf | 128/2.1 R |

FOREIGN PATENT DOCUMENTS 1298423 12/1972 United Kingdom ................. 128/2.1 R

OTHER PUBLICATIONS

Watson, "Field Collection . . . Electro-Ejaculation" Australian Veterinary Journal, vol. 40, Apr. 1964, pp. 183–187.
Gneco et al., "A New Apparatus . . . Work Physiology," Med. & Biol. Eng., vol. 9, No. 6, pp. 705–710, 1971.

*Primary Examiner*—Lee S. Cohen
*Attorney, Agent, or Firm*—Hill, Van Santen, Steadman, Chiara & Simpson

[57] ABSTRACT

A hand-held instrument is illustrated wherein a counting cycle may be initiated by pressing the active electrode against a tooth to be examined. A digital to analog converter controls a battery operated current source to supply stimulating current pulses whose intensity is linearly increased in steps at the counting rate, independently of the electrical resistance presented by the external current flow path. The counter controls an indicator which displays the successive output current values, and displays the last reading for a predetermined time interval at the end of the counting cycle.

4 Claims, 3 Drawing Figures

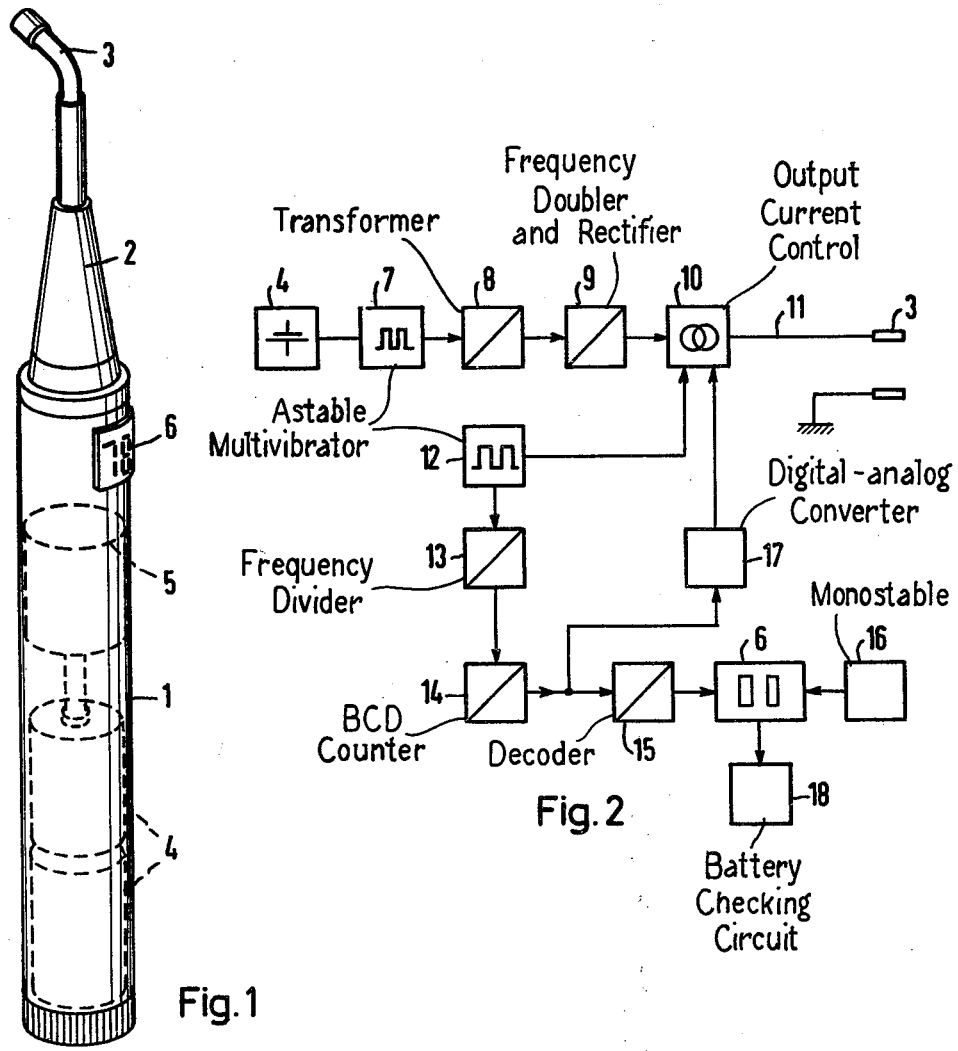
Fig. 1
Fig. 2
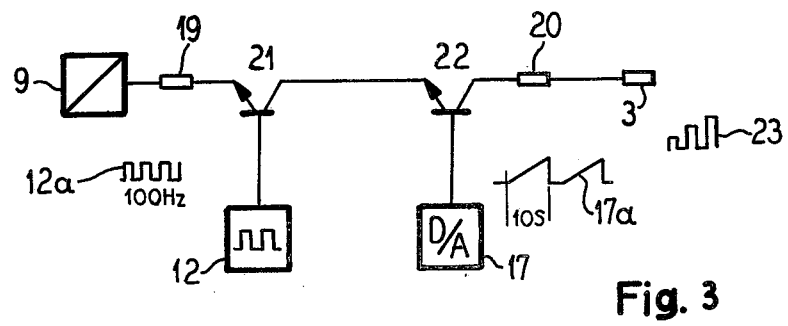
Fig. 3

ELECTRICAL PULP TESTING INSTRUMENT

BACKGROUND OF THE INVENTION

The invention relates to an electrical pulp testing instrument comprising a handpiece to accommodate a charge storage device, such as a battery as source of supply and an electrical circuit arrangement to generate a stimulating current variable as to its strength.

In an instrument known from prior art (U.S. Pat. No. 3,943,919) the stimulating current is varied by way of a potentiometer which is to be adjusted manually by means of a knurled disc arranged externally at the handpiece. This kind of adjustment of the intensity requires a relatively high consumption of current, on the one hand, on account of the potentiometer inserted as compensating resistance and on the other hand because of the connecting time left to the physician based on the individual manual operation. The consequence of the increased current consumption is that the charge storage means in the handpiece must be replaced and/or recharged more frequently than desirable. Because of the patient resistance fluctuating very much from patient to patient and the transfer resistance between electrode and tooth, moreover, no satisfactory linearity can be accomplished in the setting of the intensity. The patient and transfer resistances placed parallel with the setting resistance for regulating the intensity in fact are relatively high and thus exert a non-negligible influence on the output current of the pulp testing instrument.

SUMMARY OF THE INVENTION

The objective of the invention is to eliminate these disadvantages. According to the invention the teaching in this respect is to provide means in a pulp testing instrument of the initially mentioned kind which automatically step up the stimulating current during a predetermined period of time from zero to a maximum value linearly and disconnect the current at the expiration of this period.

Advantageous embodiments and improvements of the invention are recited in the dependent claims. An embodiment of the invention is explained more in detail by way of the accompanying sheet of drawings. Other objects, features and advantages will be apparent from this detailed disclosure and from the appended claims.

BRIEF DESCRIPTION OF THE DRAWINGS

FIG. 1 shows a dental pulp testing instrument in a graphic representation;

FIG. 2 shows a block circuit diagram of the electronic circuitry to generate the variable stimulating current; and FIG. 3 shows an exemplary circuit for the output current control component of FIG. 2.

DETAILED DESCRIPTION

FIG. 1 shows in graphic representation a dental pulp testing instrument comprising a handpiece 1 with a testing head 2 including the active electrode 3 being arranged at the anterior end of the handpiece. Two batteries 4 are inserted as source of supply in the housing of the handpiece 1 for electronic circuitry identified in the figure by 5. Reference numeral 6 identifies an indicating member showing the intensity of the stimulating current delivered at the testing tip 3.

FIG. 2 shows the block circuit diagram of the circuitry. The battery voltage of the charge storage device 4 of about 5 to 8 volts DC is chopped in an astable multivibrator 7 into a frequency of five kilohertz ($f_1=5$ KC). The rectangular voltage thereby obtained is stepped up by a transformer 8 to approximately 30 times this value and doubled and rectified in a frequency doubler circuit 9 to about 200 volts. The high voltage thus generated is fed into an electronic constant current source 10, whose output 11 is connected to the active electrode 3.

The constant current source 10 is scanned with a frequency of one hundred hertz ($f_2=100$ cycles per second) which is generated by a second astable multivibrator 12. The constant current source assures the function of the pulp testing instrument independently of the patient's resistance and/or the transfer resistance at the point of contact of the active electrode at the tooth to be examined.

Reference numeral 13 designates a frequency divider which converts the 50 cycles per second supplied thereto by the astable multivibrator 12 to five hertz ($f_3=5$ cycles per second). The output of the frequency divider 13 is connected to a binary coded decimal (BCD) counter 14 which counts the impulses delivered by the frequency divider 13 and offers at the output a binary coded decimal (BCD) signal. The binary coded decimal (BCD) counter 14 is followed by a decoder 15 which forms a signal from the coded signals, by which signal it is possible to directly control the indicator member identified by 6 in FIG. 1. The indicator member 6 is here a liquid crystal with a seven-segment indication. Component 16 is a monostable circuit (monoflop) which stores the intensity value indicated in the indicator member 6 for a certain period of time $t=3$ seconds. The stored value is erased after the expiration of this period. The output of the binary coded decimal counter 14 controls a digital-analog converter 17 connected to the constant current source 10. The digital-analog converter 17 is practically the timing member for an automatic stepping up of the output current (stimulating current) from zero to a maximum value of about 100 microamperes. The converter 17 is so designed that its peak value is reached after about ten seconds. Then the pulp testing instrument is disconnected. Finally, 18 identifies a battery checking system causing the indicator member 6 to blink at a visible frequency when the battery voltage drops below a determined minimum value. A corresponding circuitry arrangement for this is described in German patent application P 26 40 216.

It is an essential advantage of the pulp testing instrument according to the invention that the output current is completely independent of the patient resistance and/or the transfer resistance at the point of measurement and varied linearly. The regulation of the intensity is automatic, that is, when the apparatus is turned on, which can be done by pressing the active electrode against the tooth to be examined, a linear increase of the intensity commences automatically. After about ten seconds when the possible peak value of 100 microamperes has been reached, the instrument automatically disconnects. The digital reading is produced during the stepping up and stored after the disconnecting for about three seconds by the monoflop 16. This allows even after the disconnecting of the instrument still a sufficiently long time for a good reading.

As a result of the elimination of the rheostat required in the pulp testing instruments according to prior art it is possible to considerably reduce the current consumption. Both the electronic constant current power source and the automatic intensity adjustment during a predetermined period of time also contribute toward this. The indication of readiness for operation necessary heretofore by way of an incandescent lamp likewise may be dispensed with because the digital indication is operative during the operation. This likewise makes possible a reduction of the current consumption.

FIG. 3 shows an exemplary circuit for the constant current source or output current control component 10 of FIG. 2. The constant current source essentially consists of two resistances 19 and 20 and two transistors 21 and 22. Transistor 21 is pulsed with the 100 Hz pulse waveform 12a from multivibrator 12. Transistor 22 regulates the stimulation current intensity in accordance with the output waveform 17a from converter 17 to supply the stimulation current pulse waveform 23, each pulse of waveform 23 being switched on and off according to waveform 12a at the 100 Hz rate, and the amplitude of the successive current pulses of waveform 23 increasing linearly according to the input pulse rate to counter 14, over the cycle (of ten seconds duration) of successively higher output values of waveform 17a. The progressive rise in stimulation current from zero up to 100 microamperes is thereby achieved at active electrode 3, with the desired 100 Hz switching frequency.

Where the counter 14 is to count fifty counts and the indicator 6 is to display fifty different values of stimulation current corresponding thereto, for example between zero and 98 microamperes, the counter 14 may be made to count by twos, for example by supplying the input count pulses to the second binary stage of counter 14 so that the indicator 6 displays successive even count values 2, 4, 6, . . . 96, 98 as the counter receives forty-nine input pulses. The fiftieth input pulse may then serve to reset the counter to 00 and the carry pulse from the counter may serve to trigger the monostable circuit 16. Actuation of monostable 16 may serve to block further counting of input pulses, the zero count in the counter causing the converter 17 to supply an output which maintains transistor 22, FIG. 3, in a nonconducting state.

If monostable 16 is to cause continued display of the count value ninety eight, the monostable output may be coupled to two decimal lines of the decoder 15 representing the count values ninety and eight, or the corresponding binary coded decimal lines, or the monostable output may be coupled directly to the driver stages for the six segments required to display a nine in the tens position of indicator 6, FIG. 1, and to the seven segments for displaying an eight in the units position. The completion of a cycle and consequent actuation of monostable 16 would thus result in the display of the final stimulus current value of ninety eight for the desired time interval.

It will be apparent that many modifications and variations may be effected without departing from the scope of the novel concepts and teachings of the present invention.

We claim as our invention:

1. An electrical pulp testing instrument comprising a handpiece having means accommodating a charge storage device as source of supply, and electrode means, and an electrical circuit means operable to generate a stimulating current variable as to its strength, said electrical circuit means being connected to said electrode means for supply of said stimulating current thereto, said electrical circuit means having circuit means (10, 14, 17) which automatically step up the stimulating current during a predetermined period of time from zero to a maximum value linearly and disconnect the current at the expiration of said period, characterized by said step up circuit means comprising an electronic constant current source (10), said electrical circuit means comprising a chopper (7) connected with the accommodating means, a transformer (8) connected with the output of the chopper, and rectifier means connected with the output of said transformer and having its output connected with said constant current source (10) for energizing said constant current source (10), an astable multivibrator (12) connected with said constant current source (10) for switching the current output thereof at a constant frequency ($f_2$), a frequency divider (13) connected to the multivibrator (12), said step up circuit means further comprising a binary coded decimal counter (14) connected to the output of the frequency divider (13), and a digital-analog converter means (17) connected with the counter for actuation thereby to produce a progressively changing output and connected to the constant current power source (10) for sequencing the step up of the stimulating current.

2. The pulp testing instrument as defined in claim 1 characterized by providing a digital indicating member (6) connected with said step up circuit means (10, 14, 17) for indicating the intensity of the stimulating current.

3. The pulp testing instrument as defined in claim 2, characterized by the presence of a monostable means (16) connected with said indicating member (6) for controlling the same to display the intensity value indicated during a certain period of time ($t_1$) and then to erase it.

4. The pulp testing instrument as defined in claim 1, characterized by a decoder (15) connected to the output of the counter (14), and a seven-segment indicator member (6) controlled by the output signal of said decoder.

* * * * *